United States Patent [19]
Briggs, III

[11] Patent Number: 5,649,534
[45] Date of Patent: Jul. 22, 1997

[54] ENDOTRACHEAL TUBE BITE BLOCK AND ANTI-BITE ASSEMBLY

[76] Inventor: Stephen W. Briggs, III, P.O. Box 1503, Orangevale, Calif. 95662

[21] Appl. No.: 660,797

[22] Filed: Jun. 6, 1996

[51] Int. Cl.⁶ .................................................. A61M 16/00
[52] U.S. Cl. ........................ 128/207.14; 128/207.17; 128/200.26; 128/911; 128/861; 128/DIG. 26; 604/178
[58] Field of Search ................. 128/207.14, 207.17, 128/200.26, 911, 912, DIG. 26, 861; 600/238; 604/174

[56] References Cited

U.S. PATENT DOCUMENTS

| | | |
|---|---|---|
| 4,896,667 | 1/1990 | Magnuson . |
| 5,334,186 | 8/1994 | Alexander ................. 604/178 |
| 5,355,874 | 10/1994 | Bertram .................. 128/200.26 |
| 5,395,343 | 3/1995 | Iscovich ................. 128/DIG. 26 |

*Primary Examiner*—Vincent Millin
*Assistant Examiner*—V. Srivastava
*Attorney, Agent, or Firm*—Donald E. Nist

[57] ABSTRACT

The improved endotracheal bite block includes an elongated bite tube having a central endotracheal tube-receiving cavity extending therethrough to the front and rear ends of the bite tube. The bite tube is relatively inflexible and has an elongated post extending rearwardly thereof. The post has a strap-receiving slot therein and a rear retaining wall extending laterally outwardly for releasably holding an adhesive strip in place on the bite block, which tape also is used to hold an endotracheal tube against the bite block. The bite block further includes an elongated flexible strap with a strap retainer at one end and an opposite free end which can be passed through the slot and around an endotracheal tube and then can be cinched up to anchor the endotracheal tube and bite block together. Preferably, the bite tube is C-shaped in cross-section and single walled. One embodiment includes the bite block abutting a strip of adhesive tape wound around the endotracheal tube adjacent the front end thereof and with the strap cinched over the adhesive strip. Another embodiment includes the bite block abutting the adhesive tape strip and with a second strip of the tape wrapped around the first tape strip and also around the post forward of the retaining wall. Preferably, the bite block is plastic and the strap has a roughened surface on one or two opposite sides of the strap.

8 Claims, 2 Drawing Sheets

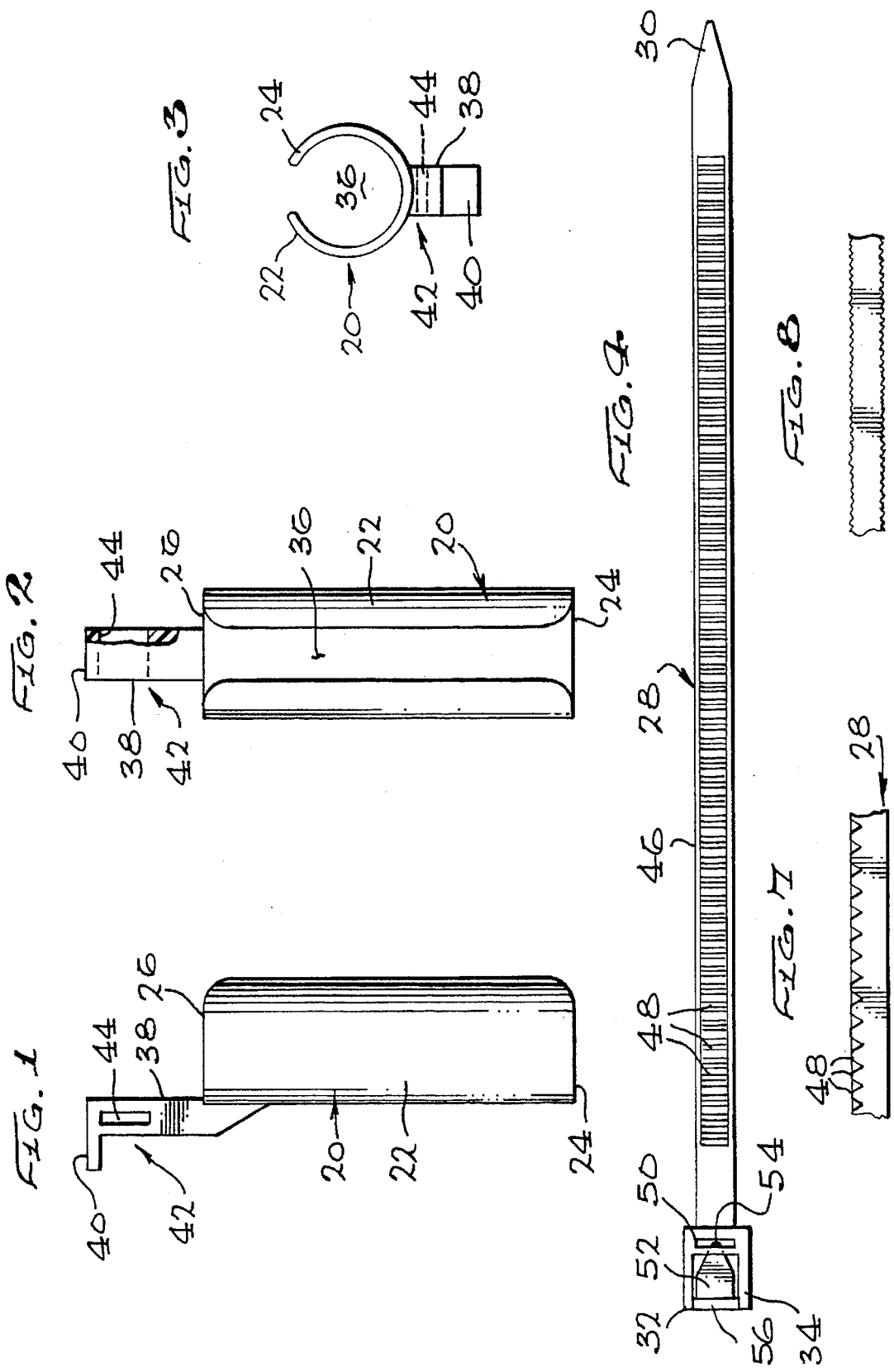

ENDOTRACHEAL TUBE BITE BLOCK AND ANTI-BITE ASSEMBLY

BACKGROUND OF THE INVENTION

1. Field of the Invention

The present invention generally relates to medical devices and more particularly to an improved bite block for an endotracheal tube and to an assembly incorporating the bite block and endotrachial tube.

2. Prior Art

Various devices have been proposed to prevent a patient's teeth from clamping down on an endotracheal tube, thus pinching the tube and restricting or entirely cutting off the flow of oxygen or air to the patient's lungs through the endotracheal tube. Many trauma victims of motor vehicle accidents and the like suffer neurological impairment. One result is a tendency to clamp down and bite into an endotracheal tube inserted in the victim's mouth. Reduction of the flow of air or oxygen to such a patient in an emergency situation may critically impair chances for the patient's recovery.

Moreover, the patient may bite hard enough to rupture the pilot balloon which is normally disposed in the endotracheal tube to seal the tube and thereby assure a closed system with air or oxygen being supplied to the patient's lungs in an adequate but controlled amount. When the balloon is ruptured, oxygen or air can leak around the tube causing inadequate ventilation and possible hypoxemia. If this occurs, it is then necessary to replace the endotracheal tube in order to reacquire the necessary closed ventilation system.

One endotracheal tube bite block known in the art is that disclosed in U.S. Pat. No. 4,896,667 to Magnussen. The Magneussen bite block comprises a hard inner tube and a softer outer tube secured to the upper end of the inner tube. Such bite block has several drawbacks, including inadequate means for securing the bite block to the exterior of an endotracheal tube. Moreover, the bite block is relatively expensive to manufacture, since it must be fabricated of materials of two separate flexibilities which must be assembled together. The lower end of the tube is squared off or slightly tapered and difficult to secure to an endotracheal tube by tape or the like.

Various other bite blocks are known in the art but generally are complicated in design and difficult and costly to make and/or difficult to assemble and connect to an endotracheal tube.

Accordingly, there is a need for an improved type of endotracheal tube bite block which is simple in design, easy to make and use, inexpensive and readily and securely attachable to an endotracheal tube in various ways, depending on the particular protocol required. There is also a need for an improved assembly of the bite block and endotrachial tube.

SUMMARY OF THE PRESENT INVENTION

The improved endotracheal tube bite block and assembly of the present invention satisfy all the foregoing needs. The bite block and assembly are substantially as described in the ABSTRACT OF THE DISCLOSURE.

Thus, the bite block can be formed in a single step plastic forming operation from readily available inexpensive materials such as plastic, compression-resistant rubbber or the like. It comprises, in combination, an elongated rigid bite tube which can be single walled in a C-shaped cross-sectional configuration and which integrally incorporates an elongated post extending rearwardly from the rear end of the main body of the tube and in a direction parallel to the longitudinal axis of the tube. The rear end of the post terminates in a retaining wall extending laterally outwardly of the tube, preferably at a 90 degree angle and defines with the remainder of the outer surface of the post a tape-receiving space for securely anchoring the bite block to the outer surface of an endotracheal tube.

The post adjacent its rear end defines a slot through which a flexible resilient strap is inserted for also anchoring the bite block to the exterior of the endotracheal tube. The strap has an elongated body adapted to slide through the slot and has a retainer at one end to releasably cinch up the strap. The strap has at least one rough side to facilitate the cinching up and releasable securing of the strap in place around an endotracheal tube. The strap may have two opposite roughened sides, the second side acting to engage and grip the exterior of the endotracheal tube to prevent slippage between the strap and endotracheal tube.

In one embodiment of the invention, an anti-bite endotracheal tube assembly is provided which comprises the bite block fitted around an endotracheal tube and abutting a strip of adhesive tape wound around the endotracheal tube. The bite block is secured to the endotracheal tube by the bite block strap passing through the post slot and around the adhesive strip and cinched tight by the strap retainer.

In another embodiment of the invention, an anti-bite endotracheal tube assembly is provided which differs from the just-described assembly in that a second strip of adhesive tape is wound around the bite block post and the first strip. The strap is not used in this assembly.

Further aspects of the present invention are set forth in the following detailed description and accompanying drawings.

DRAWINGS

FIG. 1 is a schematic side elevation of a preferred embodiment of the improved endotracheal tube bite block of the present invention;

FIG. 2 is a schematic front elevation, partly broken away, of the bite block of FIG. 1;

FIG. 3 is a schematic bottom plan view of the bite block of FIG. 1;

FIG. 4 is a schematic top plan view of the strap utilizable in the bite block of FIG. 1;

FIG. 7 is a schematic enlarged fragmentary side elevation of the strap of FIG. 4, showing its corrugated surface;

FIG. 8 is a schematic enlarged fragmentary side elevation of a modified form of the strap utilizable with the bite block of the present invention, the strap showing roughened opposite surfaces;

Figure 5:
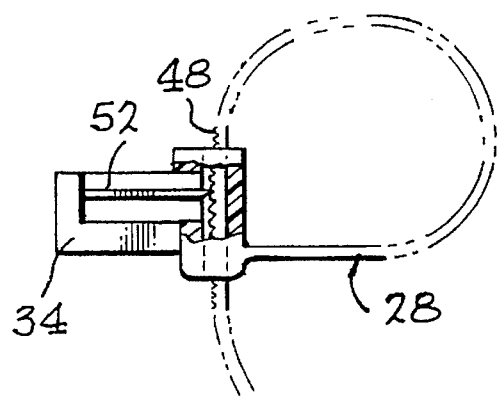
FIG. 5 is a schematic fragmentary side elevation of the strap of FIG. 4, showing the strap releasably secured by its retainer.
Figure 6:
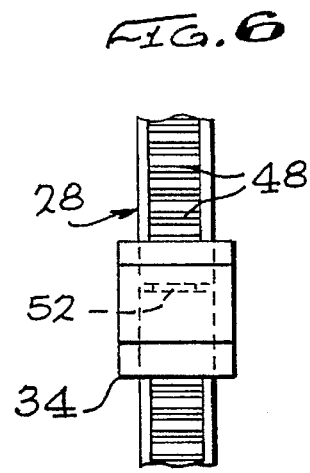
FIG. 6 is a schematic fragmentary front elevation of the retainer portion of the strap of FIG. 4.
Figure 9:
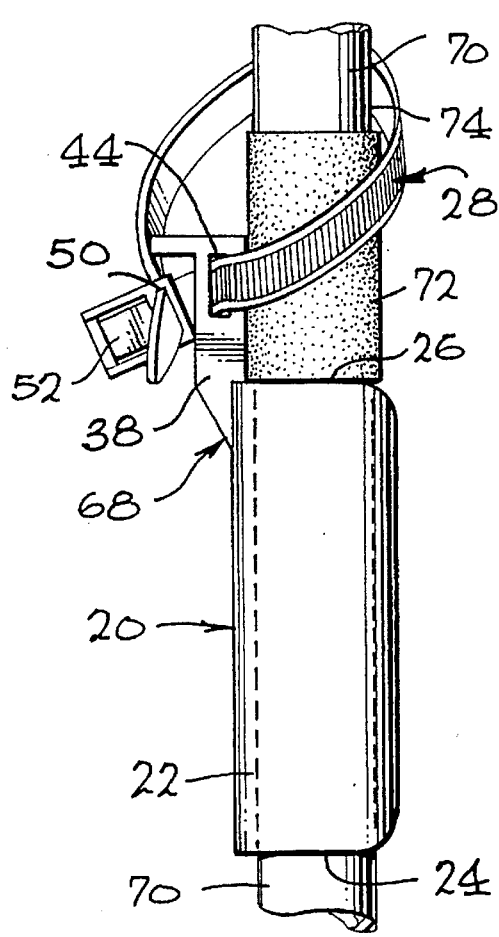
Figure 10:
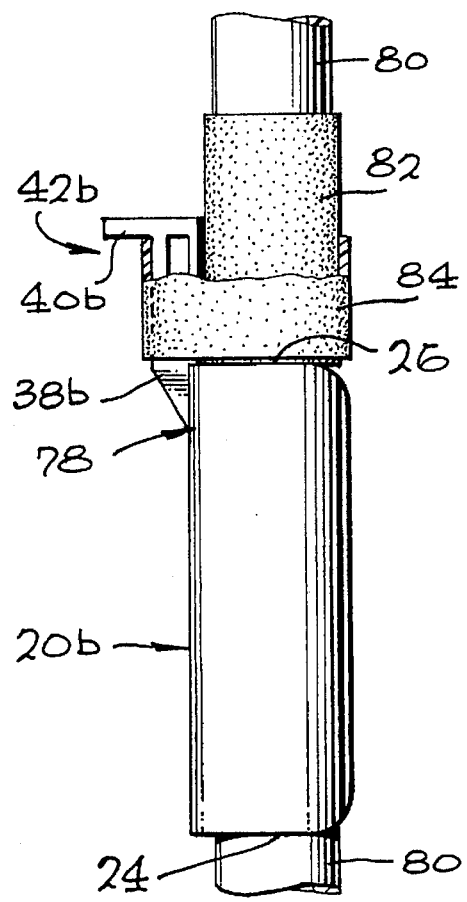

FIG. 9 is a schematic fragmentary side elevation of a first preferred embodiment of the assembly of the present invention, showing the bite block abutting a strip of adhesive tape wound around the endotracheal tube and with the bite block strap cinched around the tape; and, FIG. 10 is a schematic fragmentary side elevation of a second preferred embodiment of the assembly of the present invention, showing the bite block abutting a first strip of adhesive tape wound around the endotracheal tube and with a second strip of the tape wound around the first strip of tape and the bite block post.

DETAILED DESCRIPTION

FIGS. 1–7.

Now referring more particularly to FIGS. 1–7 of the drawings, a preferred embodiment of the improved entdotrachial tube bite block of the present invention is schematically set forth therein. Thus, bite block 20 is shown, which comprises, in combination, a generally cylindrical, relatively inflexible, preferably C-shaped (in cross-section) elongated tube 22 having a front end 24 and an opposite rear end 26, and an elongated, preferably flat, flexible and resilient strap 28 having a pointed free end 30 and an opposite end 32 bearing a specially shaped strap retainer 34.

Preferably, tube 22 and strap 28 are of plastic, rubber (hardened rubber in the case of tube 22) or the like. Tube 22 is preferably single-walled and defines a central cavity 36 extending therethrough and within which an endotrachial tube (not shown) can be slip fitted. Tube 22 is strong and resistant to pinching or crushing by a patient's teeth, but has some slight "give" to it, that is, is very slightly resilient, so as to resiliently forcefully grip the endotracheal tube.

Tube 22 has an integral post 38 extending rearwardly from the rear end 26 of the main body of tube 22. Post 38 extends parallel to the longitudinal axis of tube 22 and has a rear end 40 which extends laterally outwardly therefrom, preferably at about a 90 degree angle to said longitudinal axis. Rear end 40 forms an abuttment against which a strip of adhesive tape (not shown) can be braced to help hold the strip of tape in place. Rear end 40 together with the outer surface of post 40 which is forwardly thereof form a tape strip-receiving area generally designated 42.

Post 38 also defines a slot 44 extending transversely therethrough. Strap 28, except for retainer 34, can pass through slot 44. Strap 28 has a flat side 46 bearing spaced transversely extending parallel grooves 48 therein, which grooves 48 facilitate releasably locking strap 28 in place around an endotrachial tube by retainer 34.

Retainer 34 has a slot 50 extending therethrough and in communication with an integral resilient retainer key 52. Key 52 has a pointed front end 54 which releasably engages grooves 48 and a rear end 56 which when depressed biases front end 54 out of grooves 48, thus providing the desired releasable cinching mechanism for strap 28. If desired, entire strap 28, including retainer 34 can be integral and formed in a single forming operation at low cost. Retainer 34 enables strap 28 to be looped around the exterior of an endotrachial tube and cinched releasably tightly to firmly hold bite block 20 in place around the endotrachial tube.

Thus, bite block 20 has two separate useful means for anchoring it to an endotrachial tube, namely, strap 28 and post 38, which not only bears slot 44 for strap 28, but also tape-receiving area 42, for improved efficiency in joining bite block 20 to an endotrachial tube. Moreover, bite block 20 can be made inexpensively, is durable, positively prevents deformation of an endotrachial tube by a patient attempting to bite on block 20 and is easy to attach to an endotrachial tube and remove it therefrom.

FIG. 8.

A modification of the strap of the present invention is set forth schematically in FIG. 8. Thus, a portion of strap 28a is shown, which is identical to strap 28, except that it bears a roughened surface, as by sandblasting or the like, on flat side 46a and also on the opposite flat side 60. Roughened side 60 helps to better anchor strap 28a to the exterior of an endotrachial tube or to a strip of adhesive tape or the like wound around such endotrachial tube. Strap 28a can be fabricated of the same materials as strap 28.

FIG. 9.

A first preferred embodiment of an improved anti-bite endotrachial tube assembly of the present invention is set forth schematically in FIG. 9. Thus, assembly 68 is shown. It includes bite block 20 shown in place around an endotrachial tube 70, rear end 26 of tube 22 abutting a strip 72 of adhesive tape wound around the outer surface 74 of tube 70, and with strap 28 passing through slot 44 in post 38 and slot 50 in retainer 34 for cinching strap 28 tightly against surface 74 and/or strip 72, thus holding tube 70 and block 20 firmly together, for an improved result. Thus, bite block 20, tube 70 and strip 72 form assembly 68.

FIG. 10.

A second preferred embodiment of the improved anti-bite endotrachial tube assembly of the present invention is schematically depicted in FIG. 10. Thus, assembly 78 is shown. It includes block 20b which is identical to block 20 but minus strap 28. Block 20b is disposed around endotrachial tube 80 and abuts a first strip of adhesive tape 82 wound around tube 80. A second strip 84 of adhesive tape is wound around strip 82 and post 38b and abuts end 40b in tape-receiving area 42b to hold tube 80 and bite block 20b firmly together. Thus, assembly 78 includes bite block 20b, tube 80 and strips 82 and 84. Assembly 78 has improved utility over conventional bite block-endotrachial tube assemblies.

Various other modifications, changes, alterations and additions can be made in the improved bite block and assembly of the present invention and in the components and parameters thereof. All such modifications, changes, alterations and additions as are within the scope of the appended claims form part of the present invention.

What is claimed is:

1. An endotracheal tube bite block, said block comprising, in combination:

a) an elongated substantially rigid bite tube having open opposite front and rear ends and a central cavity extending between and communicating with said ends for slidably receiving an endotracheal tube through said rear end, and an elongated post integral with and extending rearwardly from said rigid tube rear end generally parallel to the longitudinal axis of said rigid bite tube, said post having a front end connected to said tube rear end and a rear end terminating in a retaining wall extending laterally of said rigid bite tube, said post and the retaining wall forming a tape receiving surface defined as an outer surface for securing said bite tube by a tape to an endotracheal tube, said post defining a slot extending transversely therethrough; and, b) a flexible, resilient strap having an elongated body adapted to slide through said slot, a free end and an opposite end having a retainer of larger diameter than said slot, said retainer for releasable receiving and locking said free end, whereby said body can be looped around and cinched tightly against an endotracheal tube to hold said endotracheal tube against said bite tube.

2. The bite block of claim 1 wherein said bite tube has a smooth outer surface and wherein said strap body has at least one roughened surface to facilitate engagement with said retainer.

3. The bite block of claim 2 wherein said bite tube is generally C-shaped in transverse cross-section, with a single curved wall forming said bite tube.

4. The bite block of claim 1 wherein said post retaining wall is at about a right angle to the longitudinal axis of said bite tube and wherein said bite block comprises plastic.

5. The bite block of claim 2 wherein said strap body is generally flat with opposite upper and lower surfaces and wherein said upper and lower surfaces are roughened to facilitate said releasable locking to said retainer and non-slipping engagement of said strap with the outer surface of at least one of an endotracheal tube and adhesive tape disposable around an endotracheal tube.

6. An anti-bite endotracheal tube assembly, said assembly comprising, in combination:

a) an endotracheal tube having a front end and an opposite rear end:

b) a strip of adhesive tape having a front end and an opposite rear end, said adhesive tape being wound around said endotracheal tube adjacent said front end of said endotracheal tube; and, c) a bite block releasably secured to said endotracheal tube, said bite block comprising i. an elongated generally rigid bite tube having opposite front and rear ends and a central cavity communicating with said front and rear ends of said bite tube and receiving said front end of said endotracheal tube, with the front end of said adhesive strip abutting the rear end of said bite tube, said bite tube having a post extending rearwardly therefrom and generally parallel to the longitudinal axis of said bite tube, said post having a front end and an opposite rear end, the rear end of said post extending laterally outwardly from said bite tube to form an adhesive tape retaining wall, said post also defining a slot, and, ii. a flexible resilient strap having an elongated body with a free end and an opposite end to which is secured a retainer of larger diameter than said slot, the free end of said strap passing through said slot and around said adhesive tape and being releasably cinched tightly against said adhesive tape by said retainer to lock said bite tube to said endotracheal tube.

7. The assembly of claim 6 wherein said bite block comprise plastic and wherein said bite tube is C-shape in transverse cross-section and single walled.

8. An endotracheal tube and bite block assembly, said assembly comprising, in combination:

a) an elongated endotracheal tube having a rear end and an opposite front end;

b) a first strip of adhesive tape having a front end and an opposite rear end, said adhesive tape being wound around the exterior of said endotracheal tube adjacent the front end of said endotracheal tube;

c) a bite block comprising an elongated bite tube having a front end and opposite rear end and a central cavity receiving said front end of said endotracheal tube, the rear end of said bite tube having an elongated post extending rearwardly thereof generally parallel to the longitudinal axis of said bite tube, said post having a rear end terminating in a retaining wall extending laterally outwardly from said bite tube, said post and retaining wall forming a tape receiving surface defined as an outer surface, the rear end of said bite tube abutting the front end of said first strip of adhesive tape; and, d) a second strip of adhesive tape wound around said first strip of adhesive tape and over the outer surface of said post in front of said retaining wall to releasably hold together said bite block and said endotracheal tube.

* * * * *